United States Patent [19]

Robinson et al.

[11] 4,192,824

[45] Mar. 11, 1980

[54] AROMATIC HYDROCARBON RESINS

[75] Inventors: Joseph G. Robinson, Winchcombe; David I. Barnes, Cheltenham, both of England

[73] Assignee: Coal Industry (Patents) Limited, London, England

[21] Appl. No.: 2,173

[22] Filed: Jan. 9, 1979

Related U.S. Application Data

[63] Continuation of Ser. No. 834,995, Sep. 20, 1977, abandoned.

[30] Foreign Application Priority Data

Sep. 23, 1976 [GB] United Kingdom ............... 39707/76
May 10, 1977 [GB] United Kingdom ............... 19552/77

[51] Int. Cl.$^2$ .......................... C07C 5/14; C07C 15/28
[52] U.S. Cl. ......................................585/409; 585/426
[58] Field of Search ........................ 260/668 R, 671 R

[56] References Cited

U.S. PATENT DOCUMENTS

| | | | |
|---|---|---|---|
| 2,477,538 | 7/1949 | Badertscher et al. | 260/671 R |
| 2,881,226 | 4/1959 | Wadsworth | 260/668 R |
| 3,959,226 | 5/1976 | Schmerling | 260/668 R |

*Primary Examiner*—Veronica O'Reefe
*Attorney, Agent, or Firm*—Stevens, Davis, Miller & Mosher

[57] ABSTRACT

A method of producing a condensation product by reacting together an aromatic hydrocarbon with a carbonyl compound having more than one carbon atom (therefore excluding formaldehyde) in the presence of aluminium chloride or bromide, at a temperature of from 5° to 90° C. The aluminium chloride or bromide should be substantially anhydrous. The aromatic hydrocarbon should be mono- or bi-nuclear and may be alkylated. The carbonyl compound may be an aldehyde or a betone and may be albyl or aryl.

9 Claims, No Drawings

AROMATIC HYDROCARBON RESINS

This is a continuation of application Ser. No. 834,995 filed Sept. 20, 1977, now abandoned.

This invention concerns a method of making aromatic hydrocarbon-carbonyl compound condensation products, and also concerns products made by such a method.

It has been proposed to react aromatic hydrocarbons with aldehydes having less than four carbon atoms in the presence of an acid catalyst, usually sulphuric acid. We have now found that under these conditions an aromatic hydrocarbon-aldehyde resin can only be obtained if the aldehyde is formaldehyde. In many, if not all, other cases the product of the reaction is a self condensate of the aldehyde, probably formed by a series of acid catalysed aldol-type condensations. The aromatic hydrocarbon is left substantially unreacted, and may act as a solvent for the aldol condensate.

It has now been discovered that it is possible to form aromatic hydrocarbon-aldehyde condensation products from a greater range of aldehydes than hitherto by careful selection of reaction conditions. It has also been discovered that under the same conditions it is possible to form aromatic hydrocarbon-ketone condensation products.

Therefore, according to the present invention there is provided a method of producing an aromatic hydrocarbon-carbonyl compound condensation product, comprising reacting at a temperature of from 5° to 90° C. a mixture of mono- or bi-nuclear aromatic hydrocarbon with a carbonyl compound having more than one carbon atom in the presence of substantially anhydrous aluminum chloride or bromide.

It is known to make aromatic hydrocarbon-aldehyde condensation products using formaldehyde, and therefore no claim is made to the use of formaldehyde. Therefore, whenever herein a carbonyl compound or an aldehyde is mentioned it is to be understood that these terms do not comprise formaldehyde.

It is essential to the invention to use either aluminium chloride or aluminium bromide, since these are the only two of the common Lewis acid catalysts which, under the above conditions promote the desired condensation reaction instead of the aldol-type condensation reaction.

Preferably, the aromatic hydrocarbon is either toluene or naphthalene. However such aromatic hydrocarbons as xylenes, alkyl and polyalkyl benzenes, e.g. ethyl benzenes and alkyl and polyalkyl naphthalenes may also be used. Conveniently, the alkyl groups on the aromatic hydrocarbon are not highly branched and contain up to six carbon atoms.

The carbonyl compounds may be aliphatic or aromatic. Preferably, the aliphatic carbonyl compounds have up to six alkyl carbon atoms, and are preferably not highly branched on the carbon atom(s) $\alpha$ to the carbonyl carbon. If the $\alpha$ carbon atom(s) is/are highly branched the reaction may be sterically hindered and only proceed at a very slow rate.

Preferred carbonyl compounds include acetaldehyde, propionaldehyde, butyraldehydes, benzaldehyde, acetone, ethylmethylketone and diethyl ketone. Nonetheless other carbonyl compounds such as caproaldehyde, lauraldehyde, stearaldehyde, hexan-2-one, acetophenone and propiophenone may also be used.

Such compounds as trimethylacetaldehyde and 1-trimethylacetone are preferably not used.

The most preferred carbonyl compounds are propionaldehyde, isobutyraldehyde, acetone, and benzaldehyde.

Conveniently, the molar ratio of aluminium chloride or bromide to carbonyl compound is greater than 0.5 and is preferably greater than 1. The most preferred ratio is about 1:1.

Conveniently, the molar ratio of carbonyl compound to the aromatic hydrocarbon is less than 2, and is preferably less than 1. The most preferred ratio is about 0.5.

If the above ratios are used it ensures that there is no substantial formation of aldol condensates, although it is probable that in every reaction some aldol condensate will be formed. However, using the above ratios the amount of aldol condensate will normally be not more than about 10% of the total reaction product.

Conveniently the reaction is carried out at a temperature of 40° C. or above. If the carbonyl compound used is propionaldehyde or acetone the preferred reaction temperature is about 80° C.

Preferably the reaction is terminated by adding the reaction mixture to an excess of water to hydrolyse any remaining aluminium chloride or bromide. It has been found that by controlling the temperature of the water this method of reaction termination can affect the yield of useful products from the reaction.

For example in making a toluene-aldehyde condensation product more dialkyl anthracene derivatives are produced if the water is at room temperature than if the water is at ice temperature. At ice temperature more linear polymers (vide infra) are formed.

The reaction gives rise to a dark viscous liquid containing linear dimers, trimers, tetramers and higher oligomers of the aromatic hydrocarbon formed with bridges derived from the carbonyl compound. The reaction product may also comprise species in which aromatic units are joined in their o-positions to give polycyclic structures. Among the most useful of these products are such compounds as alkyl anthracenes, derived from mononuclear hydrocarbons such as toluene.

The reaction product also comprises species in which the aromatic hydrocarbon is substituted with alkyl groups derived from the carbonyl compound, and minor amounts of species which are linearly bridged and/or alkylated polycyclic systems.

It is thought that the following reaction scheme indicates how the various species in the reaction product may be formed. However, we do not wish to be limited to such a theory, and the invention resides in the method and its products, regardless of the mechanism of the chemical reactions.

Hereinbelow R, R' and R" each represent independently hydrogen, an alkyl group or an aryl group, provided that R and R' are not both hydrogen, and X represents chlorine or bromine. The reaction scheme is only illustrated by a mononuclear aromatic hydrocarbon reaction, but it is supposed that the same scheme will hold for a binuclear hydrocarbon.

It is postulated that under these conditions the following reactions occur.

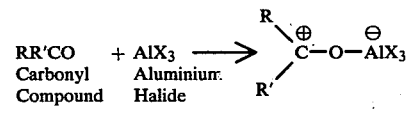

-continued

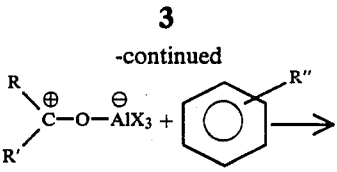

Aromatic Hydrocarbon

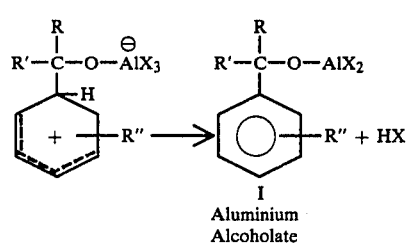

Aluminium Alcoholate

Aluminium alcoholates are known to be active intermediates in the Friedel-Crafts alkylation of hydrocarbons, decomposing with the elimination of AlOX to yield intermediate haloderivatives of the hydrocarbons. Consequently, it is supposed that the compound of general formula I is similarly converted to the haloderivative of general formula II, which is then converted to a substituted methane of the general formula III by a Friedel-Crafts reaction.

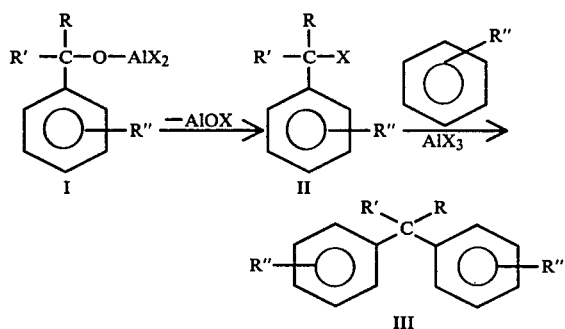

Further reaction of a compound of the general formula III with the carbonyl compound would be expected to lead to the formation of an anthracene derivative of the general formula IV as follows.

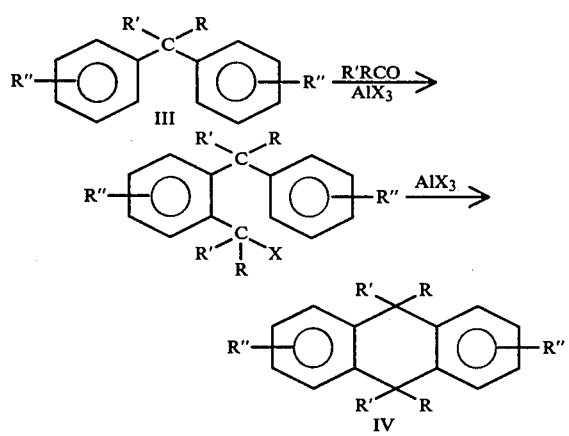

The eventual loss of an alkyl group from each of the 9 and 10 positions of the anthracene derivative leads to the formation of 2,6- or 2,7- dialkyl (R″), 9,10- dialkyl (R or R′) anthracenes. If the original carbonyl compound is an aldehyde (either R or R′=H) the product is a 2,6- or 2,7- dialkyl anthracene of the general formula V.

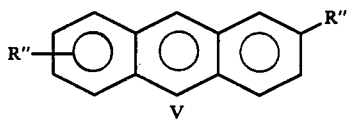

In addition to ring closure leading to polycyclic derivatives as shown above, the compounds of the general formula III may also react with free aromatic hydrocarbon to yield higher molecular weight linear products of the general formula VI, or products having more nuclei joined thereon in similar fashion.

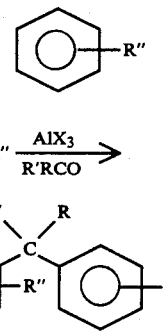

Similar bridging may also take place with polycyclic derivatives already formed as shown above (compounds of the general formulae IV or V).

Generally, the reaction product contains predominantly compounds of the general formulae III, V and VI. The relative amounts of these products depends very largely on the conditions of hydrolysis following the aromatic hydrocarbon-carbonyl compound condensation reaction.

If desired, the condensation product may be fractionated by any well known technique, for instance fractional distillation (preferably under reduced pressure), gel filtration chromatography, or solvent extraction.

The condensation products made by the method of the present invention are compatible with epoxide resins and may be used, suitably in an amount of up to 100% by weight based on the epoxide resin to extend the resin. Extended epoxide resins may be used as adhesives, in epoxide putties, as surface coatings, or for preparing laminates.

Alternatively, the components of the condensation product having alkyl substituents, such as dialkyl anthracenes, may be oxidised by conventional methods to give dicarboxyl derivatives, such as 2,6- or 2,7- dicarboxy anthraquinone. The oxidised components may then be reacted with a glycol, such as ethylene- or propyleneglycol, in the presence of a condensing agent, such as sulphuric acid, hydrogen chloride, paratoluenesulphonic acid, or a mixture of antimony trioxide and calcium acetate, to give a film- or fibre-forming polyester. These polyesters may find use in the same fields as do the well known unsaturated polyesters, such as polyethylene terephthalate.

The present invention also includes the products made by the method described above.

The following Examples are given by way of illustration only and are not to be construed as limiting in any way the scope of the invention.

EXAMPLE 1

Toluene-Propionaldehyde Condensation Products

A 500 ml flanged flask fitted with a top, stirrer and thermocouple pocket was thoroughly dried by heating in an air oven at 150° C. for 4 hours and then cooled, calcium chloride drying tubes being attached to prevent the entry of moist air.

The flask was then placed in an oil bath at 42° C. and thereafter continuously purged with dry nitrogen. 98 g of anhydrous aluminum chloride was added under conditions which minimised its exposure to air. Then 123 g of sodium-dried toluene were pumped with dry nitrogen into the flask. The temperature was thereafter raised to 40° C., and the propionaldehyde, which had been re-distilled under a pressure of 20 mm Hg, was pumped with dry nitrogen into a dry pressure equalizing funnel, from which it was dripped into the reaction flask over a period of 15 minutes. The reaction was continued for 1 hour after the commencement of the addition of the propionaldehyde. Throughout the reaction, the hydrogen chloride released was carried from the flask with the nitrogen and was separated by passage through a hydrogen chloride trap.

At the end of the reaction the contents of the flask were poured, with stirring, into 800 ml of an water to hydrolyse any free aluminium chloride. The product was then filtered into a separating funnel from which the lower aqueous layer was run off. It was then water washed until neutral and thereafter distilled in a rotary evaporator at 100° C. and a pressure of 15 mm Hg. A clear distillate and a dark coloured residue were thereby obtained.

The above procedure was repeated at different reaction temperatures and employing different proportions of reactants, as recorded in Table 1.

Table 1-

Preparation and properties of the products obtained by reacting toluene with propionaldehyde in the presence of anhydrous aluminium chloride

| Mole ratio Pr/T (a) | AlCl$_3$/ Pr Mole ratio | Reaction Time (hr) | Reaction Temperature (°C.) | Res- in yield (b) (%) | Oxygen Content (%) | Number Average Molecular Weight | Notes |
|---|---|---|---|---|---|---|---|
| 0.5 | 1.1 | 1 | 80 | 41 | 0.4 | 270 | 1 |
| 0.5 | 1.1 | 1 | 60 | 58 | 0.4 | 270 | 1 |
| 0.5 | 1.1 | 1 | 40 | 60 | 0.8 | 264 | 1 |
| 0.5 | 1.1 | 1 | 20 | 59 | 1.5 | 240 | 1 |
| 0.5 | 1.1 | 1 | 5 | 32 | 4.2 | 286 | 2 |
| 0.5 | 1.1 | 1 | 0 | — | — | — | 5 |
| 0.5 | 1.1 | 5 | 40 | 66 | 0.6 | 230 | 1 |
| 0.5 | 1.1 | 2 | 40 | 67 | 0.8 | 230 | 1 |
| 0.5 | 1.1 | 1 | 40 | 60 | 0.8 | 264 | 1 |
| 0.5 | 1.1 | 0.5 | 40 | 50 | 0.7 | 230 | 1 |
| 0.5 | 1.1 | 0.25 | 40 | 67 | 0.5 | 240 | 1 |
| 2.0 | 1.1 | 1 | 40 | 34 | 2.1 | 340 | 2 |
| 1.0 | 1.1 | 1 | 40 | 52 | 0.4 | 260 | 1 |
| 0.25 | 1.1 | 1 | 40 | 76 | 0.5 | 250 | 1 |
| 0.5 | 1.0 | 1 | 40 | 58 | 1.8 | 250 | 1 |
| 0.5 | 0.9 | 1 | 40 | 64 | 0.5 | 260 | 4 |
| 0.5 | 0.5 | 1 | 40 | 43 | 0.1 | 260 | 2 |
| 0.5 | 0.25 | 1 | 40 | 18 | 7.9 | 340 | 3 |
| 0.5 | 0.055 | 1 | 40 | 6 | 9.4 | 400 | 3 |

(a)Pr denotes propionaldehyde and T denotes toluene.
(b)The yield, expressed on the weight of toluene feedstock, refers to the residue isolated after distillation in the rotary evaporator.

Notes
1. The infra-red spectra of these resins displayed only features typical of alkyl substituted aromatic hydrocarbons.
2. The infra-red spectra of these resins displayed features typical of alkyl aromatic substitution and also those characteristic of aldol condensation products.
3. The infra-red spectra of these resins displayed only features typical of aldol condensation products.
4. The infra-red spectrum of this resin displayed only a very slight absorbtion characteristic of an aldol condensate.
5. This product was expelled from the flask with explosive violence but material collected had an infra-red spectrum characteristic of aldol condensation products only.

The reaction products were analysed by infra-red spectroscopy. It can be seen from the notes to Table 1 that, providing the reaction was carried out within the conditions set out above, the reaction product was predominantly a toluene-propionaldehyde condensation product, with at most small amounts of aldol-type condensation products.

A typical product was subjected to further analysis using gas chromatography and mass spectrometry. It was shown that the product contained ditolyl propane, tolyl propyl (ditolyl propane), alkyl anthracenes, anthratolyl propanes, and other products in minor amounts. Under favourable conditions of hydrolysis, or treatment of the condensation product with water following the condensation reaction, up to 40% by weight of alkyl anthracenes was obtained. The greater yield of alkyl anthracenes was obtained when the reaction was terminated using water at room temperature.

EXAMPLE 2

In a further set of experiments the following reactants were mixed in a 500 ml flask similarly treated to that used in Example 1, and fitted with a reflux condenser. The reactants were heated to a temperature of 80° C. (±2° C.) for 5 hours.

| Toluene | 92 g |
|---|---|
| Propionaldehyde | 29 g |
| anhydrous Al Cl$_3$ | 73.5 g |

The reaction was stopped and the product treated in an analagous manner to that Example 1. The reaction product was a black viscous resin having a number average molecular weight of 260. This product was separated into three distillable fractions and a residue by fractional distillation under reduced pressure (10 mm Hg). The three distillable fractions had the properties given in Table 2.

The residue was a black solid having a number average molecular weight of 540 and represented 32% of the condensation product.

Table 2

Fractions obtained by Fractional Distillation at 10mm Hg Pressure of the Resin Product

| Fraction No. | Boiling range (°C. at 10mm Hg) | Colour | Appearance | Number ave. Mol. Wt. | Amount present in the parent resin 90 |
|---|---|---|---|---|---|
| 1 | 85–136 | orange | Viscous | 210 | 6.1 |
| 2 | 136–256 | Orange | Viscous | 260 | 48.3 |
| 3 | 136–256 | Orange | V. Viscous | 320 | 13.6 |
| Residue | — | Black | — | 540 | 32.1 |
| Total | | | | | 100.1 |

Each of the fractions was further investigated using infra-red spectroscopy, proton magnetic resonance spectroscopy (PMR) and mass spectrometry. Fraction 1 contained substantially only ditolyl propane, and fraction 2 contained substantially only dimethyl anthracenes, these latter being formed from two toluene units joined at their o- positions by alkyl bridges derived from the aldehyde. Fraction 3 contained higher homologues of ditolyl propane, predominantly those having three or four toluene rings. The residue contained predominantly higher oligomers of ditolyl propane.

In none of the fractions was there any evidence of an aldol-type condensate, thus showing that the reaction which occurred was a condensation between the toluene and the propionaldehyde, and not an aldol-type condensation which is the reaction that occurs if any other Lewis acid catalyst is used under these conditions.

EXAMPLE 3

Toluene-Isobutyraldehyde Condensation Products

Three batches of the following reactants were thoroughly mixed in 500 ml flasks fitted with reflux condensers and treated as described in Example 1, except that one reaction was carried out at 80° C. and another at 5° C. (the third being at 40° C.).

| Toluene | 92 g |
|---|---|
| Isobutyraldehyde | 36 g |
| Anhydrous $AlCl_3$ | 73.5 g |

In each case the product was a dark viscous mass having an oxygen content of approximately 0.5% w/w and a viscosity of approximately 200 centipoise at 25° C. The number average molecular weight of each product was 250, 240 and 260 respectively.

Each product was examined by infra-red and proton magnetic reasonance spectroscopy. In all three products the predominant components were 2,6- and 2,7- dimethyl anthracenes, which together accounted for approximately 40% of the reaction products, based on the weight of the toluene taken initially. The proportions of the different reaction products depended on the temperature of the water used to hydrolyse the aluminium complexed reaction products.

Other products included:

(a) ditolyl-alkyl substituted methanes such as ditolyl isopropylmethane (1:1 ditolyl 2:2 dimethyl ethane), (b) other anthracene derivatives including 2:6 dimethyl - 9:10 - dihydro diethyl anthracene, (c) alk-aryl substituted alkyl anthracenes, (d) benzene and alkyl benzenes, such as xylenes, methyl ethyl benzenes and methyl isopropyl benzenes.

In addition there was evidence that approximately 10% w/w of the product made at 5° C. was derived solely from the aldehyde in an aldol type condensation reaction.

EXAMPLE 4

Toluene-Benzaldehyde Products

The following reactants were reacted together in a 500 ml flask similar to that used in Example 1, in a manner exactly analagous to that used in Example 1.

| Toluene | 92 g | |
|---|---|---|
| Benzaldehyde | 53 g | Reaction temperature 40° C. |
| $AlCl_3$ | 73.5 g | |

The product of the reaction after 1 hour was a dark liquid which had a number average molecular weight of 260.

The product was analysed and was shown to contain predominantly 2,6- and 2,7- dimethylanthracenes. Amongst the other components of the products were a number of aryl substituted triphenylmethanes.

EXAMPLE 5

Toluene-Acetone Products

The following reactants were reacted together in a 500 ml flask similar to that used in Example 1. The method of reacting them together was analagous to that of Example 1, except that the reaction was carried out for 24 hours at a temperature of 80° C.

| Toluene | 90 g | |
|---|---|---|
| Acetone | 29 g | Reaction temperature 80° C. |
| $AlCl_3$ | 73.5 g | |

The product was a very viscous dark liquid having a number average molecular weight of 320.

The product was analysed and contained predominantly 2,6- and 2,7- dimethylanthracenes. Amongst the other components of the product were a number of substituted indanes, the five membered ring of the indane being formed by ring closure of the acetone on the toluene.

The materials made in any of the Examples given above according to the present invention are suitable as formed to be used to extend epoxide resins, but may also be separated into their components. For instance, mixtures containing substantially only 2,6- and 2,7- dimethylanthracenes have been isolated and oxidised, using acetic acid/chromic anhydride, to the corresponding anthraquinone dicarboxylic acids. These have been reacted with ethylene glycol in the presence of a mixture of antimony trioxide and calciumacetate as a condensing agent to give a polyester. The polyester was found to be film forming and could be drawn into fibres.

Thus the present invention provides a method of producing substantial yields of aromatic hydrocarbon-carbonyl compound condensation products, to the virtual exclusion of the competing aldol-type condensate normally obtained if any other acid catalyst is used under the same conditions.

We claim:

1. A method or producing an aromatic hydrocarbon-carbonyl compound condensation product, consisting essentially of the step of reacting at a temperature of from 5° to 90° C. in the presence of aluminum chloride or bromide a mixture containing as reacting components only a mono- or bi-nuclear aromatic hydrocarbon selected from the group consisting of toluene, naphthalene, xylene, alkylbenzene, polyalkyl benzene, alkyl naphthalene and polyalkyl naphthalene wherein the alkyl group is not highly branched and contains up to six carbon atoms and a carbonyl compound having more than one carbon atom.

2. A method according to claim 1, in which the aromatic hydrocarbon is toluene or naphthalene.

3. A method according to claim 1, in which the carbonyl compound is selected from the group consisting of propionaldehyde, isobutyraldehyde, benzaldehyde and acetone.

4. A method according to claim 1, in which the molar ratio of aluminium chloride or bromide to carbonyl compound is about 1.1:1.

5. A method according to claim 1, in which the molar ratio of carbonyl compound to aromatic hydrocarbon is about 0.5:1.

6. A method according to claim 1, in which the reaction is carried out at a temperature of from 40° to 90° C.

7. A method according to claim 1, and including the step of terminating the reaction by adding the reaction mixture to an excess of water.

8. A method of producing an aromatic hydrocarbon-aldehyde condensation product consisting essentially of the step of heating at a temperature of from 70° to 90° C. a mixture of propionaldehyde and a mono- or bi-nuclear aromatic hydrocarbon selected from the group consisting of toluene, naphthalene, xylene, alkylbenzene, polyalkyl benzene, alkyl naphthalene and polyalkyl naphthalene wherein the alkyl group is not highly branched and contains up to six carbon atoms in the presence of substantially anhydrous aluminium chloride.

9. A method of producing an aromatic hydrocarbon-aldehyde condensation product consisting essentially of the step of reacting at a temperature of from 5° to 80° C. a mixture of iso-butyraldehyde and a mono- or bi-nuclear aromatic hydrocarbon selected from the group consisting of toluene, naphthalene, xylene, alkylbenzene, polyalkyl benzene, alkyl naphthalene and polyalkyl naphthalene wherein the alkyl group is not highly branched and contains up to six carbon atoms in the presence of substantially anhydrous aluminium chloride or bromide.

* * * * *